United States Patent
Ramon-de-Jesus

(10) Patent No.: US 9,050,330 B2
(45) Date of Patent: Jun. 9, 2015

(54) METHOD, COMPOSITION AND KIT FOR TREATING FREQUENT HEADACHES

(71) Applicant: Jose C. Ramon-de-Jesus, Dorado, PR (US)

(72) Inventor: Jose C. Ramon-de-Jesus, Dorado, PR (US)

( * ) Notice: Subject to any disclaimer, the term of this patent is extended or adjusted under 35 U.S.C. 154(b) by 0 days.

(21) Appl. No.: 13/706,521

(22) Filed: Dec. 6, 2012

(65) Prior Publication Data

US 2014/0163072 A1  Jun. 12, 2014

(51) Int. Cl.
- *A01N 43/38* (2006.01)
- *A61K 31/40* (2006.01)
- *A61K 31/445* (2006.01)
- *A61K 31/167* (2006.01)
- *A61K 31/196* (2006.01)
- *A61K 45/06* (2006.01)
- *A61K 31/192* (2006.01)
- *A61K 31/407* (2006.01)
- *A61K 31/603* (2006.01)

(52) U.S. Cl.
CPC .............. *A61K 31/445* (2013.01); *A61K 31/167* (2013.01); *A61K 31/196* (2013.01); *A61K 45/06* (2013.01); *A61K 31/192* (2013.01); *A61K 31/407* (2013.01); *A61K 31/603* (2013.01)

(58) Field of Classification Search
None
See application file for complete search history.

(56) References Cited

U.S. PATENT DOCUMENTS

| 4,886,493 | A | 12/1989 | Yee | |
| 5,939,425 | A * | 8/1999 | Caruso | 514/289 |
| 6,432,986 | B2 | 8/2002 | Levin | |
| 6,526,318 | B1 | 2/2003 | Ansarinia | |
| 7,799,337 | B2 | 9/2010 | Levin | |
| 8,224,438 | B2 | 7/2012 | Levin | |
| 2007/0054843 | A1* | 3/2007 | Yeomans et al. | 514/9 |
| 2010/0030188 | A1* | 2/2010 | Xia | 604/514 |

* cited by examiner

*Primary Examiner* — Craig Ricci
*Assistant Examiner* — Jared R Barsky
(74) *Attorney, Agent, or Firm* — Walter O. Alomar

(57) ABSTRACT

Methods, compositions and kits for treating a headache in a human patient are provided. The methods comprise intranasally administering to the patient a composition comprising a short-acting local anesthetic, a long-acting local anesthetic and a non-steroidal anti-inflammatory drug. A composition useful for practicing the methods of the disclosure is described which comprises a short-acting local anesthetic, a long-acting local anesthetic and a non-steroidal anti-inflammatory drug, wherein the composition is formulated for intranasal delivery. A kit comprising the composition and an intranasal applicator and a method of systemically delivering the composition to a human patient is also included in the disclosure. The headache-treating effectiveness of a local anesthetic in a Sphenopalatine Ganglion Block (SFGB) is significantly enhanced by coadministering diclofenac.

1 Claim, 5 Drawing Sheets

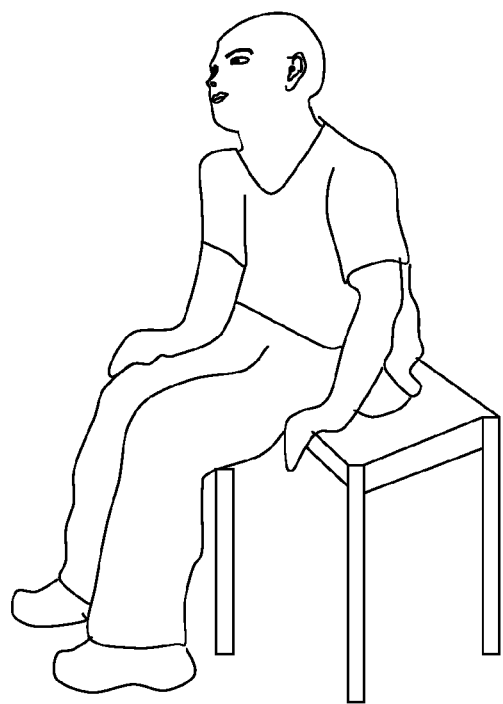
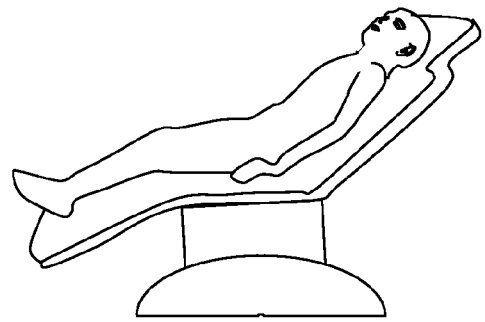
Fig. 5A
Fig. 5B

METHOD, COMPOSITION AND KIT FOR TREATING FREQUENT HEADACHES

STATEMENT REGARDING FEDERALLY SPONSORED RESEARCH AND DEVELOPMENT

N/A

RELATED APPLICATIONS

N/A

BACKGROUND OF THE DISCLOSURE

1. Field of the Disclosure

The present invention relates to methods, compositions and kits for treating frequent headaches. More particularly, this invention is concerned with alleviating frequent headache by intranasal administration of a local anesthetic together with a non-steroidal anti-inflammatory drug that blocks the formation of prostaglandin.

2. Discussion of the Background

A headache is a very common, recurring condition that is characterized by pain anywhere in the head or the neck. This disorder affects millions of Americans daily. The term "headache" includes migraines, cluster headaches, tension headaches, trigeminal neuralgia, cranial neuralgia and facial pain.

Infrequent headaches are commonly treated with oral administration of analgesics such as acetaminophen or non-steroidal anti-inflammatory drugs (NSAIDs). However, frequent or recurrent headaches have numerous causes and in most cases it is very difficult to determine. Oral administration of analgesics is not an effective way to treat frequent or recurrent headaches. Furthermore, the prolonged use of analgesics can be detrimental to the health of the patient. For instance, NSAIDs relate to adverse effect in the gastrointestinal and/or renal system of the patient. Also, daily use of analgesics can perpetuate the headache disorder. Thus the overuse of analgesics can be itself the cause of headaches. Generally analgesics should not be used for more than 15 days per month.

Methods for the treatment of recurrent headaches include: yoga, hypnosis, relaxation treatments, meditation, amongst others. However in many cases these treatments turn out to be unsuccessful. Also most of the patients that suffer from frequent headaches spent a significant amount of money and time trying to determine the cause of the headaches with different studies such as radiographies, brain scan, magnetic resonance, electroencephalography, amongst others, without any success.

An alternative treatment for headaches is a process called Sphenopalatine Ganglion Block (SPGB). The first SPGB was reported by Greenfield Sluder in which the process consisted in a transnasal administration of a cotton-tipped applicator dipped in 90% watery solution of cocaine hydrochlorate for a period of five minutes into the sphenopalatine ganglion.

The sphenopalatine ganglion, also known as Meckel's ganglion, is located in the pterygopalatine fossa, posterior to the middle nasal turbinate under a 1-1.5 mm layer of connective tissue and mucous membrane and anterior to the pterygoid canal. The sphenopalatine ganglion comprises the largest cluster of sympathetic neurons in the head outside of the brain. It also has major branches to the trigeminal nerve, the facial nerve, the carotid plexus and the superior cervical ganglion.

It is understood that the sphenopalatine ganglion serves as an important way of transmission of pain. The SPGB consists in stopping the nerve impulses of the sphenopalatine ganglion by administering a local anesthetic. This type of treatment may be referred to as a nerve block.

Additionally, other conditions or diseases such as headache disorders and other neurological conditions can be arrested, or improved by local anesthetic blockade, and/or other pharmacological augmentation or mechanical alteration of the sphenopalatine ganglion and surrounding structures.

The first SPGB performed by Sluder used cocaine as the local anesthetic. Over time, some other anesthetics have been used instead of cocaine to perform the SPGB. For instance, U.S. Pat. No. 4,886,493 discloses an SEGE using lidocaine, a shorter-acting local anesthetic. However, U.S. Pat. No. 6,432,986 discloses that the use of a shorter-acting local anesthetic such as lidocaine merely decreases head pain for a period equal to the duration of the analgesia which is a approximately less than an hour. U.S. Pat. No. 6,432,986 discloses an SPGB using long-acting local anesthetics such as ropivacaine or bupivacaine which provides anesthesia to the nerve structure for at least about an hour. U.S. Pat. No. 6,432,986 posits that these long-acting local anesthetics provide head pain relief even after the period of anesthesia.

However, the frequency of recurrence or rebound continues to be a major problem within the art. A significant number of patients continue to have recurrent headaches after been treated with an SPGB using long-acting local anesthetics. The frequency of recurrence could be a few hours or days. Thus, there is still a need to provide a composition which reduces the frequency of recurrence or rebound.

SUMMARY

The present disclosure overcomes the limitations of the previous by providing a composition comprising of lidocaine, bupivacaine and diclofenac for treating frequent headaches and which reduces the frequency of recurrence. The short-acting local anesthetic (e.g. lidocaine) is used to provide an immediate pain relief, the long-acting local anesthetic (e.g. bupivacaine) provides a long acting relief as disclosed in U.S. Pat. No. 6,432,986 to Levin here included by reference, and the non-steroidal anti-inflammatory drug (e.g. diclofenac) works as both a lubricant to perform better the SPGB and as an enhancement agent that reduces the frequency of recurrence by blocking the formation of prostaglandin.

Accordingly, it is an object of the present disclosure to provide a composition that enhances the headache treating effectiveness of a local anesthetic in an SPGB.

Accordingly, it is an object of the present disclosure to provide a composition that significantly enhances the headache treating effectiveness of a local anesthetic by reducing the frequency of recurrence.

It is another object of the present disclosure to provide a method for treating headaches comprising the intranasal administration of a composition comprising of lidocaine, bupivacaine and diclofenac to block the nerve impulses of the sphenopalatine ganglion.

Another object of the present disclosure is to provide a method for treating headaches comprising a nerve block treatment of the sphenopalatine ganglion with a composition comprising of a non-steroidal anti-inflammatory drug in gel form which serves as a lubricant in order to facilitate the insertion of the intranasal applicator.

It is another object of the present disclosure to provide a method for treating headaches comprising a nerve block treatment of the sphenopalatine ganglion with a composition comprising a non-steroidal anti-inflammatory drug lubricant serving as an analgesic for blocking the formation of prostaglandin.

Yet another object of this disclosure is to provide a composition comprising a short-acting local anesthetic, a long-acting local anesthetic and a non-steroidal anti-inflammatory drug in gel form for the treatment of headaches.

In accordance with the principles of the present disclosure the composition comprises a short-acting local anesthetic such as lidocaine, a long-acting local anesthetic such as bupivacaine, and a non-steroidal anti-inflammatory drug and lubricant substance, such as diclofenac.

Another object of the present disclosure is to provide an effective composition for treating headaches in a SPGB in order to avoid nasal cavities' damages.

BRIEF DESCRIPTION OF THE DRAWINGS

The accompanying drawings, which are incorporated herein, constitute part of the specification and illustrate the preferred embodiment of the disclosure.

FIGS. 5A to 5C shows exemplary views of the administration of the composition to a patient in accordance with the principles of the present disclosure.

DESCRIPTION OF THE PREFERRED EMBODIMENT

Figure 1:
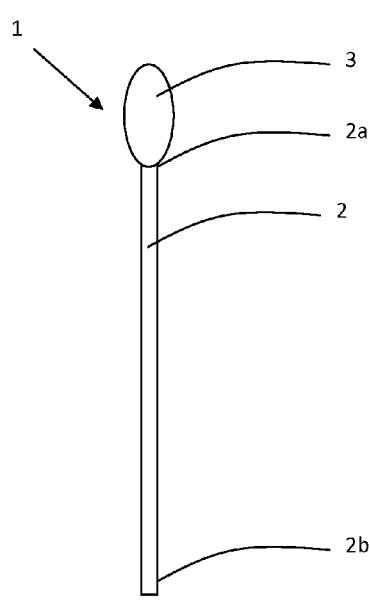
FIG. 1 shows an intranasal applicator general structure of the present disclosure in accordance with the principles of the present disclosure.

Referring to FIG. 1, the intranasal applicator comprises a shaft 2 having a first distal end 2a and a second distal end 2b, an applicator portion 3. The application portion can be made of an absorbing material such as a cotton swab or at least a material which can carry the composition for applying it to the sphenopalatine ganglion and surrounding structures. Preferably, the intranasal applicator is six inches long.

Figure 2A:
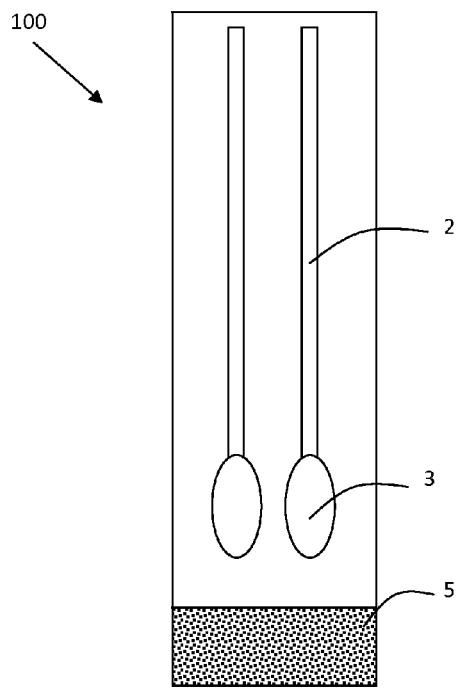
FIGS. 2A through 2B shows an exemplary embodiment of the kit of the present disclosure in accordance with the principles of the present disclosure.
Figure 2B:
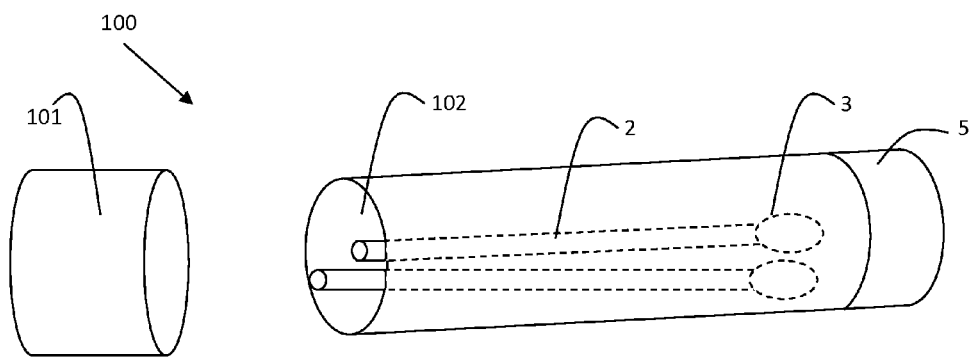

FIGS. 2A through 2B are directed to a kit 100 comprising a hollow body 102 and a cover 101. Further the hollow body 102 comprises a chamber 5 located at the opposite side of the cover 101. The chamber is used to store the composition for treating headaches.

The composition of the present invention comprises a shorter-local anesthetic such as lidocaine, a long-acting local anesthetic such as bupivacaine, and a non-steroidal anti-inflammatory drug and lubricant substance such as diclofenac.

An amount of lidocaine ranging from 0.3 ml to 0.5 ml is present in the composition. The concentration of lidocaine can range from 0.5% to 3% by weight. Our experience shows that the composition is more effective using 0.3 ml of lidocaine at 1% by weight.

An amount of bupivacaine ranging from 0.3 ml to 0.5 ml is present in the composition. The concentration of bupivacaine can range from 0.25% to 2% by weight. Our experience shows that the composition is more effective using 0.3 ml of bupivacaine at 0.5% by weight.

Compared with ropivacaine, bupivacaine is a stronger anesthetic which provides a longer period of anesthesia to the nerve structure and reduces the frequency of recurrence when mixed with a shorter-acting local anesthetic and a non-steroidal anti-inflammatory drug. Thus, bupivacaine is preferred over ropivacaine in the compositions, kits, and methods of the present invention.

An amount of diclofenac ranging from $1/20$ cc to $1/6$ cc is present in the composition. The concentration of diclofenac can range from 0.5% to 3% by weight. Our experience shows that the composition is more effective using 0.05 cc of diclofenac at 1% by weight.

The composition for treating headaches may be mixed by any agitator or even with the intranasal applicator before applying it to the sphenopalatine ganglion.

FIG. 3 through 5C are directed to the process of administering the composition to the patient.

Figure 3:
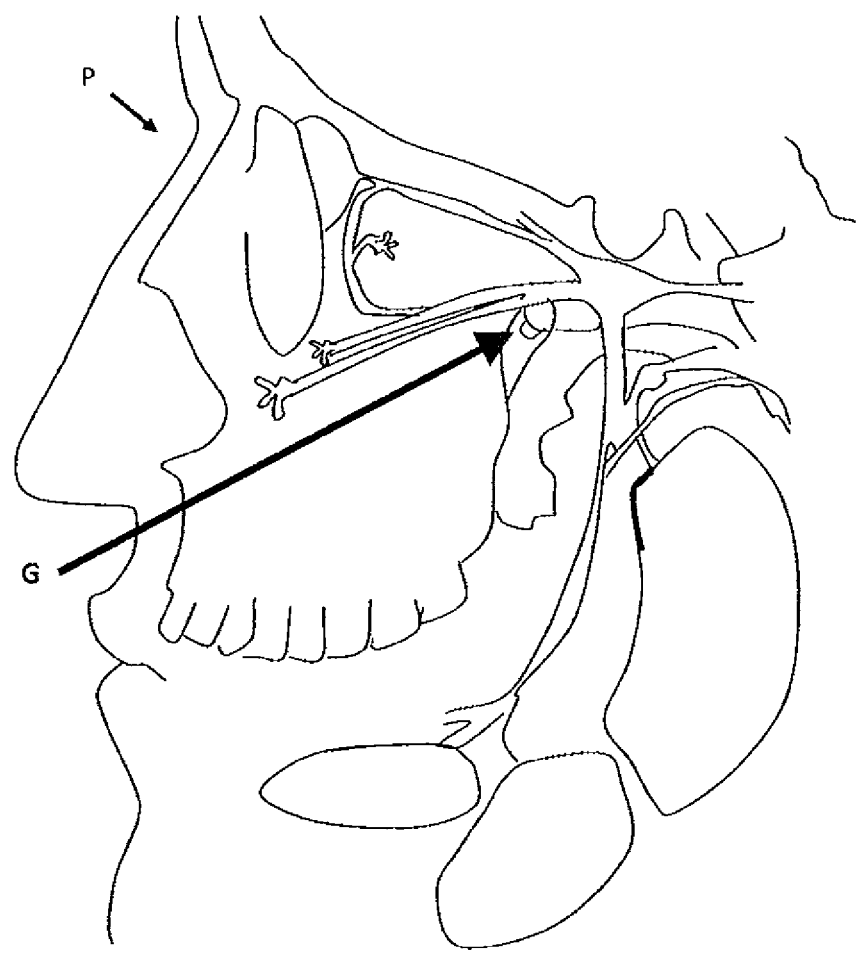
FIG. 3 shows an exemplary view of the area to be reached by the intranasal applicator in accordance with the principles of the present disclosure.

Referring to FIG. 3, the sphenopalatine ganglia G, as mentioned before, is a neuronal structure located principally in the center of the person's head P in the pterygopalatine fossa posterior to the middle turbinate. The sphenopalatine ganglion comprise the largest cluster of sympathetic neurons in the head outside of the brain.

Local anesthetics are known to block the generation and the conduction of nerve impulses by slowing the propagation of nerve impulses, and by reducing the rate of rise of the action potential of the nerve. The ability to block nerve fibers which mediate the processes involved in the headache cycle varies with the particular local anesthetic used. Short-acting local anesthetics do not exhibit the same degree of differential blockade exhibited by long-acting local anesthetics. However, even when combining short-acting local anesthetic with long-acting local anesthetic the average duration between a patient's rebound is a few hours or days.

The composition of the disclosure, administered intranasally to a patient inhibits headache's symptoms for a period of at least four days. Furthermore, in our experience in most of the cases the composition inhibits headache's symptoms for a period of at least two weeks. In a number of cases the composition inhibits headache's symptoms for a period of three months. Thus, as described herein, the composition comprising lidocaine, bupivacaine, and diclofenac is effective for alleviating headaches and in reducing the rate of rebound or recurrence.

The two anesthetics are primarily provided to block the nerve fiber as explained above and the non-steroidal anti-inflammatory drug is used to inhibit or block the formation of prostaglandin. Prostaglandins are incriminated in pain perception within the nervous system. They are produced within the central nervous system and sensitize it to painful substances. Pain is thus induced in two ways (local and central) via direct sensitization of nerve receptors by prostaglandins. While not wishing to be bound by any particular theory, it is believed that inhibiting the formation of prostaglandin when performing the SPGB enhances significantly and surprisingly the headache-treating effectiveness of the local anesthetic and, therefore, it reduces the frequency of recurrence or rebound in the patient. As mention above, in our experience the headache-treating effect of the composition last at least four days and in most of the cases last at least two weeks. Also in a number of cases the composition inhibits headache's symptoms for a period of three months.

The non-steroidal anti-inflammatory drug is preferably in gel form so that it serves also as a lubricant avoiding damages to the nasal cavities, more particularly the irritation of the nasal mucous membrane.

Non-steroidal anti-inflammatory drugs which may be used to practice the invention include diclofenac, diflusinal, etodolac, naproxen and the like.

Various dosages forms may be made which comprises 0.3 ml of lidocaine at 1%, 0.3 ml of bupivacaine at 0.5%, and 0.05 cc of diclofenac at 1%. The anesthetics and the no-steroidal anti-inflammatory drug are preservative-free in order to avoid damages to the nasal cavities or irritations. This composition is administered to each nostril of a patient for a period of 20 minutes. Thus, the complete time for the method is approximately 40 minutes.

It is important to understand that the rate of systemic absorption in a patient of a local anesthetic is dependent on the patient's tissues absorption capabilities, the total dose, the concentration, and the identity of the local anesthetic administered to the patient.

Figure 4:
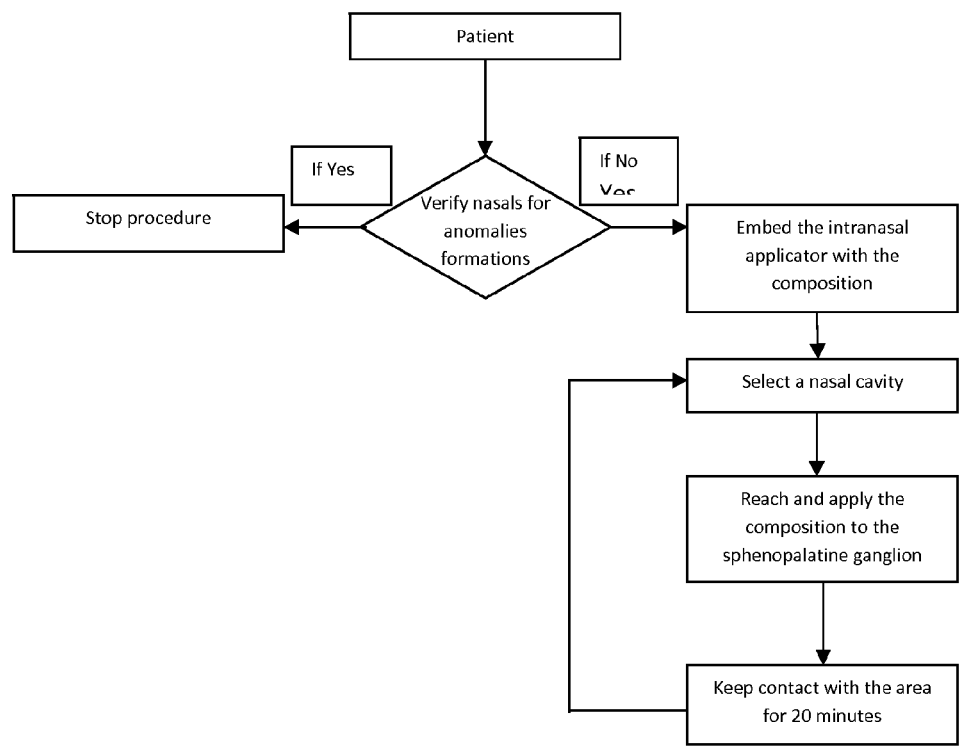
FIG. 4 shows a flowchart exemplary embodiment of the administration of the composition to a patient in accordance with the principles of the present disclosure.
Figure 5C:
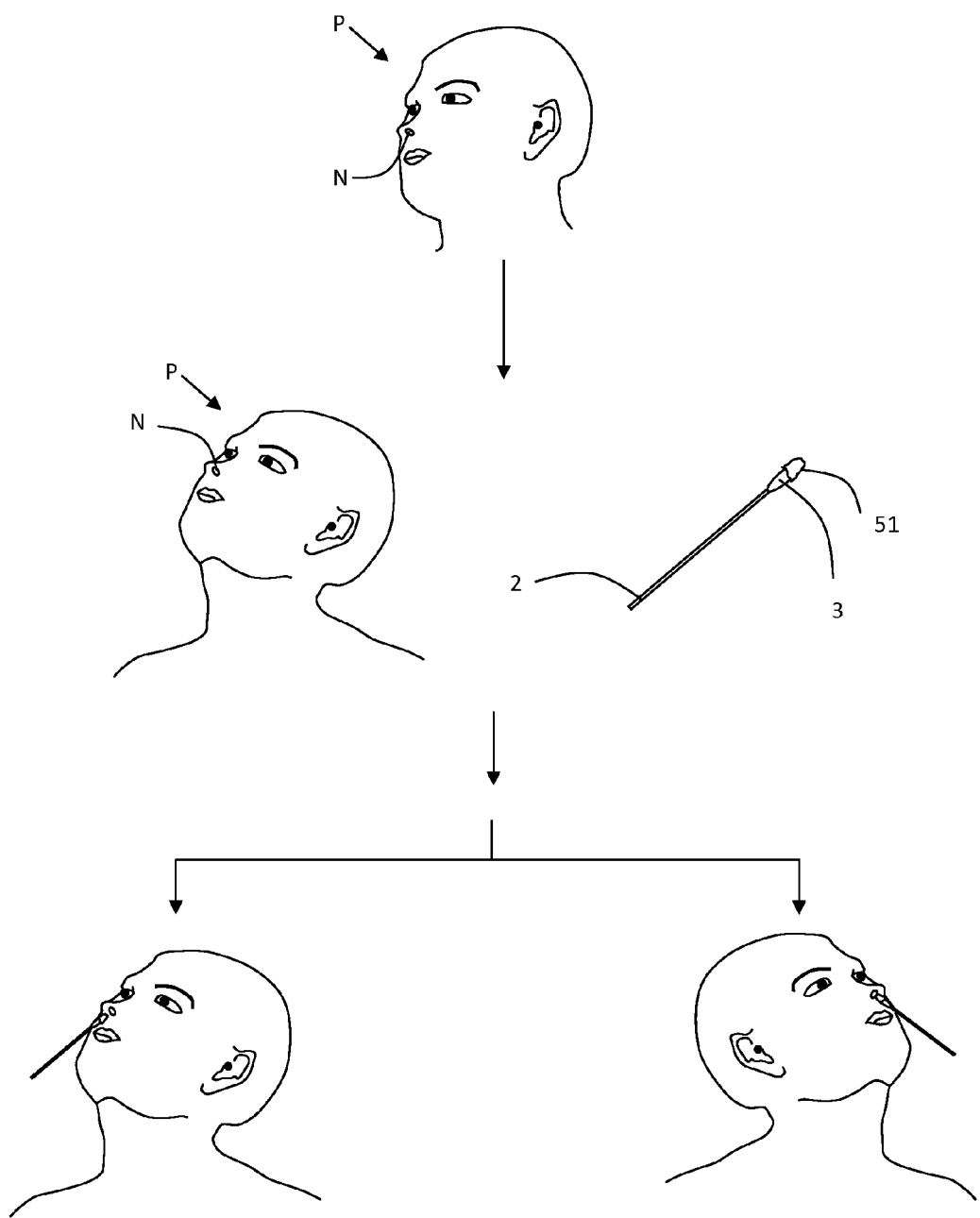

The steps of the method, as shown in FIG. 4 through FIG. 5C, are as follows:

Step 1. The patient is located at a doctor's test area. Preferably the patient is sat on a medical exam table, as shown in FIG. 5A. The patient is placed supine on the table with the cervical spine extended, as shown in FIG. 5B.

Step 2. The nasal cavities of the patient are examined with a rhinoscope to verify any abnormalities, including tumors, polyps or foreign bodies. If any abnormality is diagnosed the procedure is stopped. No other procedure can be completed until the abnormality is checked by a specialist. The purpose of verifying abnormalities in the nasal cavities is to avoid irreparable damages to the nasal cavities and to determine if the cause of the headache is due to a major disease, for instance a tumor. If no abnormalities are perceived or diagnosed the procedure continues.

Step 3. Patient head is tilted in order to provide a easy access for the physician to the sphenopalatine ganglia, as show in FIG. 5B. Simultaneously the intranasal applicator 1, more particularly the applicator portion 3 is embedded with the composition.

Step 4. The physician selects a first nasal cavity.

Step 5. The physician inserts the intranasal applicator 1 through nasal cavity N with the help of the rhinoscope and reaches the sphenopalatine ganglia G with the applicator portion 3.

Step 6. The physician holds the intranasal applicator 1 in position contacting the sphenopalatine ganglia for a predetermined period of time. The time is between 15-25 minutes, preferably 20 minutes. It is important to understand, as previously mentioned, that the systemic absorption of the patient depends on several factors. Therefore, physician should continue applying the blocking agent until the patient's pain is gone. In our experience, the headache's symptoms disappear in 20 minutes.

Step 7. After finishing with the first nasal cavity the physician repeats step 5 to step 6 on the second nasal cavity.

It is important to understand that the term physician include doctors, or any health care provider. Further, during the intranasal administration of the composition to the patient a sterile environment is preferred.

EXAMPLE 1

Intranasal Administration of a Composition Comprising Lidocaine, Bupivacaine, and Diclofenac Gel For Alleviating Frequent Headaches The purpose of the experiments described in this Example was to determine the efficacy of intranasal administration of a composition comprising lidocaine, bupivacaine, and diclofenac gel for alleviating frequent headaches. The composition was administered to patients experiencing frequent headaches including migraines, cluster headaches, tension headaches, trigeminal neuralgia, cranial neuralgia and facial pain. Most of the patients had tried other forms of therapy like oral administration of analgesics, yoga, meditation, and have been examined by other doctors and tested with different exams like radiographies, brain scan, magnetic resonance, electroencephalography, without any success. The two patients and their responses were as follows.

Patient 1

This patient was a 38-years-old male who experienced tension headaches and migraines. The pain was acute producing nauseas and vomits. The patient was treated with physic therapy, floricet, relafen and norflex without success. The patient was administered the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 9 days after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 27 days after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 3 months after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 18 days after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 18 days after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 18 days after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

Patient 2

This patient was a 35-years-old female, who experienced recurring cluster headaches and trigeminal neuralgia producing nauseas and loss of appetite. The pain was intermittent every day. The patient was administered the composition comprising 0.3 ml of lidocaine at 1%, 0.3 ml of bupivacaine at 0.5%, and 0.05 cc of diclofenac at 1%. The patient's pain disappeared after the procedure.

The patient did not have a rebound until 4 days after the procedure. The patient was administered again the composition comprising 0.3 ml of lidocaine at 1%, 0.3 ml of bupivacaine at 0.5%, and 0.05 cc of diclofenac at 1%. The patient's pain disappeared after the procedure.

What is claimed is:

1. A method for treating headaches in a human patient comprising a first intranasal administration to a patient with a composition comprising 0.3 ml of lidocaine at a concentration of 1%, 0.3 ml of bupivacaine at a concentration of 0.5% and 0.05 ml of diclofenac at a concentration of 1% with an intranasal applicator to accomplish a Sphenopalatine Ganglion Block, whereby the composition is administered to each nostril of the patient for 20 minutes to treat headaches, and a second intranasal administration to the patient after about 4 days from the first administration of said composition, whereby the composition is administered to each nostril of the patient for a period of about 15-25 minutes to treat headaches for at least two weeks.

\* \* \* \* \*